United States Patent

Berguer et al.

[11] Patent Number: 5,840,067
[45] Date of Patent: Nov. 24, 1998

[54] CENTERFLOW CATHETER

[76] Inventors: Ramon Berguer, 5865 Bloomfield Glens, West Bloomfield, Mich. 48322; Farshad Malekmehr, 1321 Orleans St. #2001, Detroit, Mich. 48207

[21] Appl. No.: 808,393

[22] Filed: Feb. 28, 1997

[51] Int. Cl.⁶ .................................................. A61M 29/00
[52] U.S. Cl. .................. 604/104; 604/107; 604/177; 604/174; 606/198
[58] Field of Search ...................... 604/96, 104–107, 604/174, 175, 177; 606/198

[56] References Cited

U.S. PATENT DOCUMENTS

| | | | |
|---|---|---|---|
| 5,135,517 | 8/1992 | McCoy | 604/105 |
| 5,279,565 | 1/1994 | Klein et al. | 604/105 |
| 5,509,900 | 4/1996 | Kirkman | 604/104 |

*Primary Examiner*—Mark Bockelman
*Assistant Examiner*—Jennifer R. Sadula
*Attorney, Agent, or Firm*—Barnes, Kisselle, Raisch, Choate, Whittemore & Hulbert P.C.

[57] ABSTRACT

A device for supporting the outlet end portion of an intravascular catheter within a blood vessel while a treating agent is delivered into the blood stream through an orifice at the tip. The device comprises a frame having a plurality of radially outwardly projecting frame elements in the form of elongated wire struts extending lengthwise of the catheter. Each wire strut has a generally V-shaped radially outwardly projecting mid-portion, with the apex of the V-shaped mid-portion adapted to rest on the wall of the blood vessel. The distal ends of the wire struts are affixed to the catheter. The proximal ends are longitudinally sidable in grooves in the catheter. The grooves are long enough to accommodate the wire struts when flattened somewhat to pass through narrower blood vessels or when flattened completely for storage in a tube shelter.

5 Claims, 2 Drawing Sheets

CENTERFLOW CATHETER

FIELD OF INVENTION

This invention relates generally to intravascular catheters and more particularly to a device for supporting the distal end portion within a blood vessel at or near the center or axis of flow within the vessel.

BACKGROUND AND SUMMARY

The present invention is particularly useful in catheters that remain in place within a blood vessel for an extended period of time, such as weeks or months. Such catheters are left in place to nourish patients who cannot be fed by mouth, or, more frequently, to administer chemotherapeutic drugs to treat cancer.

A catheter left on its own within a blood vessel tends to rest its tip against the vessel wall. This causes mechanical irritation of the vessel wall. In addition, the delivery of chemotherapeutic and other drugs against the vessel wall often causes inflammation and eventual thrombosis (clot formation) in the blood vessel. If the catheter tip is close to or in contact with the wall of the blood vessel where the flow is much slower, the undiluted chemicals delivered against the frail endothelial lining of the blood vessel will irritate it and set up local inflammation and thrombosis.

Conversely, if the catheter tip is at the center of the blood vessel, it is positioned at the axis of flow where flow is faster and chemicals delivered by the catheter tip are better mixed with blood and carried away from the wall faster. The chemical agents are also delivered at the greatest distance possible from the walls, that is, at the center of the blood vessel. What is proposed by this invention is to maintain the catheter on the axis or center of flow in the blood vessel by use of a special frame structure consisting preferably of a plurality of spring loaded, fine metal struts. These metal struts are well tolerated within the venous and arterial systems. They may, for example, be 1½ inches in length and located at the distal end of the catheter.

The wire struts are preferably fixed to the distal end of the catheter and naturally protrude outwardly, resting their "elbows" on the vessel wall and maintaining the catheter in the center. The more proximal portion of each wire strut is not attached, but moves freely along a groove or slot within the catheter wall. The wire struts may thus flex radially inward and outward depending on the diameter of the blood vessel. When the catheter is stored, a plastic tube shelter or sheath may cover the struts which are then flattened within the catheter wall and do not protrude. When the catheter is being introduced into a blood vessel, it is done by sliding it forward from the sheath. The sheath remains outside the body. As the catheter is advanced from smaller or larger diameter blood vessels, the struts deploy as required because they are spring loaded. When the catheter finally ends up in the larger central blood vessels, the struts are fully deployed.

One object of this invention is to provide a device for supporting an intravascular catheter within a blood vessel having the foregoing features and capabilities.

Another object is to provide a device for supporting an intravascular catheter within a blood vessel which is composed of a relatively few simple parts, is durable and long lasting in use, and is capable of being inexpensively manufactured and easily manipulated.

These and other objects, features and advantages of the invention will become more apparent as the following description proceeds, especially when considered with the accompanying claims and drawings.

DETAILED DESCRIPTION OF THE PREFERRED EMBODIMENT

Figure 2:
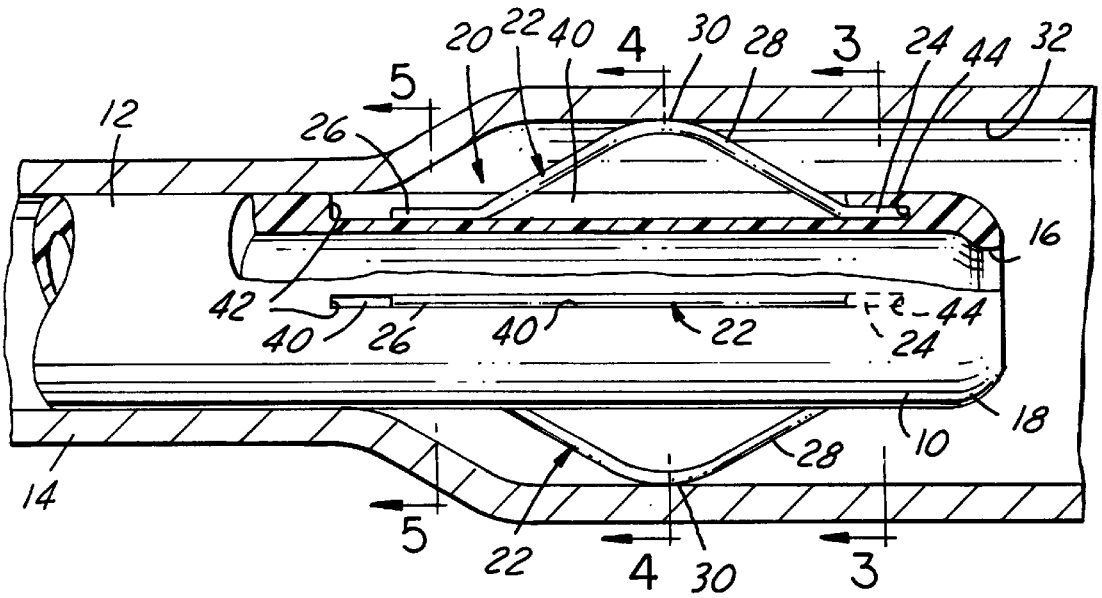
FIG. 2 is a fragmentary side elevational view showing the struts fully deployed in a larger diameter blood vessel.
Figure 3:
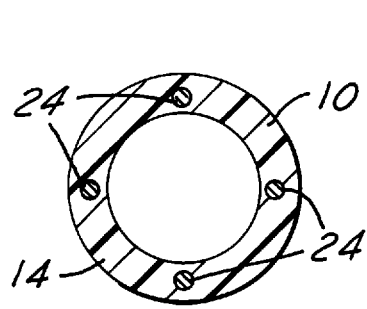
FIGS. 3, 4 and 5 are sectional views respectively taken on the lines 3—3, 4—4 and 5—5 in FIG. 2.
Figure 5:
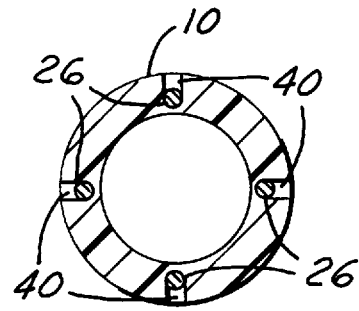
Figure 4:
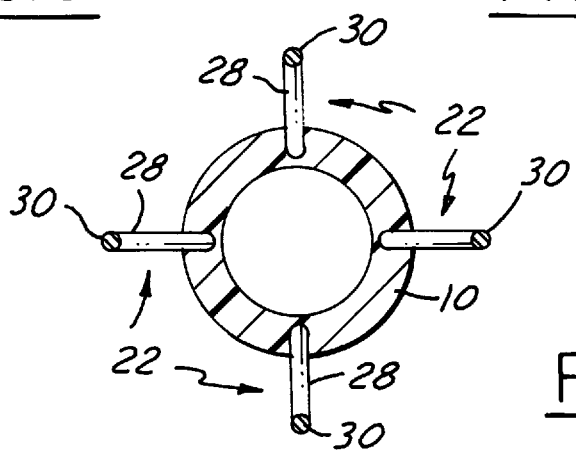
Figure 6:
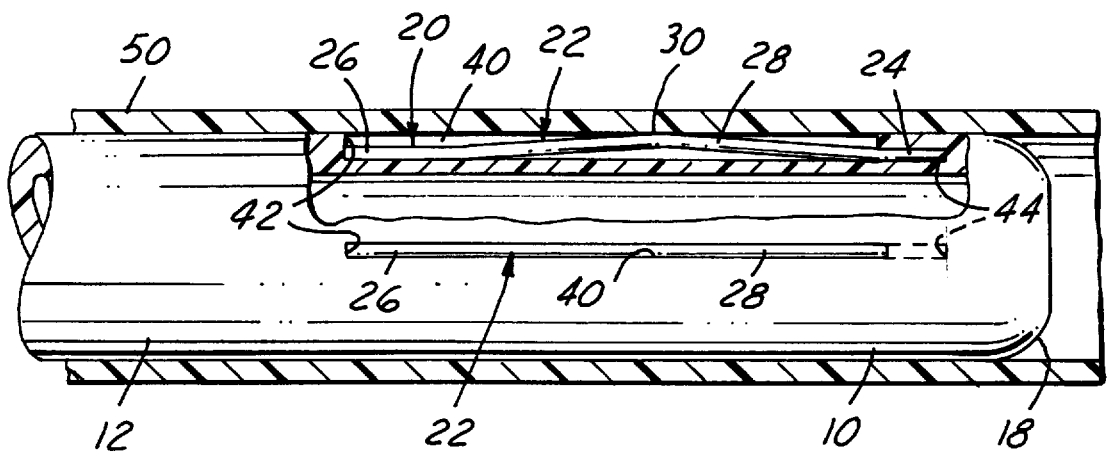
FIG. 6 is a side elevational view showing the catheter stored within a tube sheath with the struts collapsed against the wall of the catheter.

Referring now more particularly to the drawings, and especially to FIG. 2, the distal or outlet end portion 10 of a catheter 12 is shown supported within a blood vessel 14 of a patient. The catheter is a flexible tubular member having an orifice 16 at the tip 18 for the discharge of a flowable substance into the blood stream. The flowable substance may be any treating agent such as a chemotherapeutic drug or simple nourishment.

The outlet end portion 10 of the catheter is supported in the blood vessel by a frame structure 20 comprising a plurality of frame elements in the form of flexible, resilient spring-like, individual and separate, fine metal struts 22 made from a suitable material such, for example, as stainless steel or titanium. These metal struts are preferably 1–1½ inches in length and are well tolerated within the venous and arterial systems.

The wire struts are arranged in equal, angularly spaced relation about the central axis of the distal end portion 10 of the catheter and extend lengthwise of the catheter. The wire struts are of identical construction, each having a distal end 24 adjacent to the tip 18 of the catheter, a proximal end 26 more remote from the tip, and a generally V-shaped radially outwardly projecting mid-portion 28. The apex or elbow 30 of the mid-portion rests against the interior wall of the blood vessel. Preferably, the elbows press lightly and resiliently against the interior wall 32 of the blood vessel and maintain the outlet end portion 10 of the catheter parallel to the blood vessel 14 and centrally located on the axis of flow of blood in the blood vessel.

Figure 1:
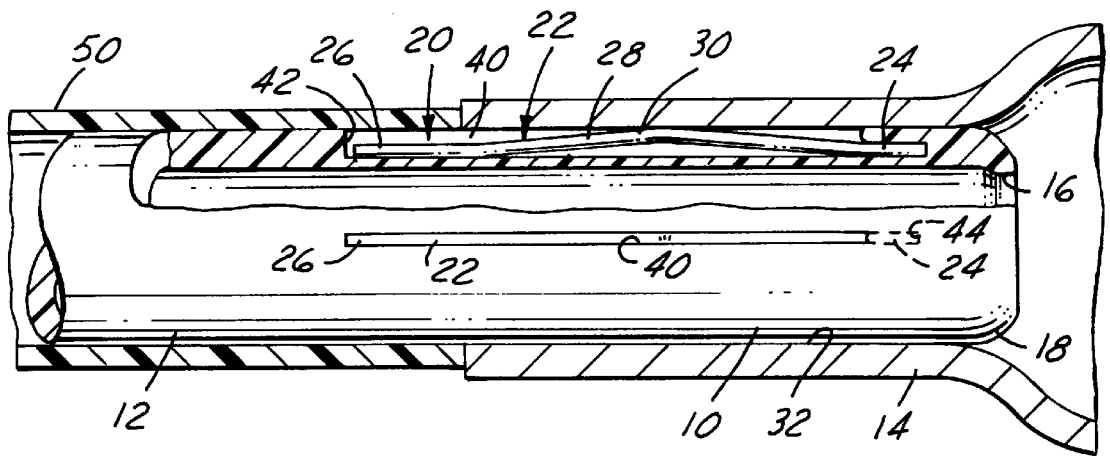
FIG. 1 is a fragmentary side elevational view with parts in section showing the distal end of an intravascular catheter being slid out of a sheath and into a blood vessel. The view shows the spring-loaded struts of the invention partially deployed and engaging the walls of the blood vessel.

The distal end 24 of each wire strut is generally parallel to the length dimension of the outlet end portion 10 of the catheter and is anchored within the body of the material of the catheter wall as shown in FIG. 1. The proximal end 26 of the wire strut is of approximately the same length as the distal end 24 and is parallel to the distal end and disposed in a longitudinal groove 40 in the exterior surface of the wall of the catheter. The groove 40 is preferably an open slot as shown and extends from one end 42 to the other end 44. The proximal end 26 of the wire strut is longitudinally slidably supported in the groove.

The wire struts are capable of being radially compressed as shown in FIG. 1 when passing through a narrower portion of the blood vessel. When compressed, the proximal ends of the wire struts will slide in the grooves 40 as may be necessary. In a larger diameter portion of a blood vessel, the struts expand but still press lightly against the vessel wall. In their natural, free state or uncompressed condition, the struts will expand somewhat beyond that shown in FIG. 2.

The elbows or apices 30 of the mid-portions of the wire struts are preferably slightly rounded or curved as shown to more easily slide along the interior surface of the blood vessel.

The catheter may be stored in a plastic tube shelter or sheath 50 of approximately the same diameter as the catheter which will cover the struts and cause them to be compressed and flattened against the catheter wall and not to protrude. The length of the grooves 40 in the catheter wall are sufficient to accommodate the proximal ends 26 and the mid-portions 28 of the struts as needed to allow for a fill collapse of the struts against the exterior surface of the catheter.

To introduce the catheter into a blood vessel, the catheter is slid in a forward direction out of the tube sheath 50 and into the blood vessel, the sheath remaining at all times outside the body (FIG. 1). The catheter may be advanced from smaller to larger diameter blood vessels and in doing so the spring-loaded struts will deploy to the extent needed to engage the interior wall of the blood vessel because of their spring loading. When the catheter finally arrives in the larger diameter central blood vessel as shown in FIG. 2, the struts are fully deployed yet still spring-loaded and bearing under light pressure against the interior wall of the blood vessel.

When the catheter is withdrawn, its path goes from the larger to a smaller diameter blood vessel, causing the walls of the smaller diameter blood vessel to close around it, and the struts to collapse to the extent necessary, sliding in the grooves 40 and allowing the catheter to exit via the small blood vessel through which it was introduced.

What is claimed is:

1. In combination, an intravascular catheter provided with an outlet end portion having a tip formed with an orifice, and a device for supporting the outlet end portion of the catheter within a blood vessel while a treating agent is delivered into the blood vessel through the orifice at the tip of said outlet end portion, said device comprising frame structure carried by and projecting radially outwardly from said outlet end portion of the catheter for engagement with the blood vessel to support said outlet end portion centrally within the blood vessel with the tip out of contact with the blood vessel, said frame structure comprising a plurality of radially outwardly projecting frame elements mounted on said outlet end portion of the catheter in angularly spaced relation thereabout, said frame elements being in the form of identical, elongated, flexible, resilient, wire struts extending lengthwise of said outlet end portion of the catheter, each said wire strut having a distal end adjacent to the tip of the catheter, a proximal end more remote from said tip, and a generally V-shaped, radially outwardly projecting mid-portion having an apex adapted to rest on a wall of the blood vessel, the mid-portion of each said wire strut being passively collapsible radially inwardly solely under the influence of radial pressure, and each said wire strut being independent of the other wire struts and free of manipulation or activation by an operator or a remote power source.

2. The combination defined in claim 1, wherein one of the ends of each of said wire struts is affixed to the outlet end portion of the catheter and the other end thereof has a longitudinally slidable engagement with said outlet end portion.

3. The combination defined in claim 1, wherein the distal end of each of said wire struts is affixed to the outlet end portion of the catheter and the proximal end thereof has a longitudinally slidable engagement with the said outlet end portion.

4. The combination defined in claim 3, wherein said outlet end portion of the catheter has a plurality of angularly spaced, longitudinally extending grooves slidably receiving the proximal ends of the respective wire struts, said grooves being sufficiently long to accommodate the proximal ends of said wire struts when the mid-portions of said struts are collapsed radially inwardly.

5. The combination defined in claim 4, wherein each of said grooves extends continuously from the distal ends of said struts to the proximal ends thereof to receive the mid-portions of said struts when said struts are collapsed radially inwardly.

* * * * *